United States Patent
Seter et al.

(10) Patent No.: US 10,258,255 B2
(45) Date of Patent: Apr. 16, 2019

(54) METHOD FOR PRODUCING A MINIATURE ELECTROMAGNETIC COIL USING FLEXIBLE PRINTED CIRCUITRY

(75) Inventors: Dan Seter, Haifa (IL); Lior Sobe, Kadima (IL); Itay Kariv, Haifa (IL)

(73) Assignee: St. Jude Medical International Holding S.àr.l., Luxembourg (LU)

( * ) Notice: Subject to any disclaimer, the term of this patent is extended or adjusted under 35 U.S.C. 154(b) by 546 days.

(21) Appl. No.: 13/232,536

(22) Filed: Sep. 14, 2011

(65) Prior Publication Data

US 2013/0066194 A1  Mar. 14, 2013

(51) Int. Cl.
| | |
|---|---|
| *A61B 5/05* | (2006.01) |
| *H05K 3/10* | (2006.01) |
| *A61B 5/06* | (2006.01) |
| *H01F 5/00* | (2006.01) |

(52) U.S. Cl.
CPC ............ *A61B 5/062* (2013.01); *H01F 5/003* (2013.01); *Y10T 29/49155* (2015.01)

(58) Field of Classification Search
CPC .... A61B 5/062; Y10T 29/49155; H01F 5/003
USPC ........................................................ 600/424
See application file for complete search history.

(56) References Cited

U.S. PATENT DOCUMENTS

| | | | |
|---|---|---|---|
| 5,153,408 A * | 10/1992 | Handford et al. | ....... 219/121.64 |
| 5,421,193 A * | 6/1995 | Carlin et al. | .................... 73/49.2 |
| 6,014,579 A | 1/2000 | Pomeranz et al. | |
| 6,073,043 A | 6/2000 | Schneider | |
| 6,233,476 B1 | 5/2001 | Strommer et al. | |
| 6,253,770 B1 | 7/2001 | Acker et al. | |
| 6,498,944 B1 | 12/2002 | Ben-Haim et al. | |
| 6,788,967 B2 | 9/2004 | Ben-Haim et al. | |
| 6,939,338 B2 * | 9/2005 | Waldhauser et al. | ......... 604/531 |
| 7,386,339 B2 | 6/2008 | Strommer et al. | |
| 7,448,909 B2 * | 11/2008 | Regnier et al. | .......... 439/607.05 |
| 7,618,266 B2 * | 11/2009 | Yamada et al. | ................. 439/90 |
| 7,816,915 B2 | 10/2010 | Susel et al. | |
| 7,844,319 B2 | 11/2010 | Susil et al. | |
| 7,881,769 B2 | 2/2011 | Sobe | |

(Continued)

FOREIGN PATENT DOCUMENTS

| | | |
|---|---|---|
| DE | 2 205 045 A1 | 8/1973 |
| EP | 0 989 384 A2 | 3/2000 |

(Continued)

OTHER PUBLICATIONS

Notification of Reason for Rejection dated Mar. 3, 2014 in Japanese Patent Application No. 2014-530356 (including English translation).

*Primary Examiner* — Michael T Rozanski
(74) *Attorney, Agent, or Firm* — Dykema Gossett PLLC (57) ABSTRACT

An elongate medical device includes a sensor configured to detect one or more characteristics of an electromagnetic field in which the device is disposed. The sensor includes an electrically-insulative substrate, rectangular in shape, and a patterned, conductive trace disposed on the substrate. The patterned trace includes a plurality of diagonal sections parallel to one another, arranged with a relatively low pitch. The substrate is wrapped into a cylindrical shape thereby forming a three-dimensional spiral capable of functioning as a micro-electromagnetic sensor. A medical positioning system is responsive to the signal from the sensor to determine a position and/or orientation of the sensor.

18 Claims, 5 Drawing Sheets

(56) References Cited

U.S. PATENT DOCUMENTS

| | | | |
|---|---|---|---|
| 7,885,707 B2 | 2/2011 | Hauck | |
| 2003/0187347 A1 | 10/2003 | Nevo et al. | |
| 2005/0283067 A1* | 12/2005 | Sobe | A61B 5/06 600/409 |
| 2007/0088416 A1 | 4/2007 | Atalar et al. | |
| 2007/0157828 A1 | 7/2007 | Susel et al. | |
| 2008/0140152 A1* | 6/2008 | Imran | A61N 1/0553 607/46 |
| 2008/0176271 A1* | 7/2008 | Silver et al. | 435/29 |
| 2009/0002958 A1* | 1/2009 | Li | H05K 3/0032 361/748 |
| 2009/0112103 A1* | 4/2009 | Kassem | 600/488 |
| 2009/0131930 A1* | 5/2009 | Gelbart et al. | 606/41 |
| 2009/0288057 A1* | 11/2009 | Pirkle | G06F 17/5077 716/128 |
| 2010/0036284 A1* | 2/2010 | Laynes et al. | 600/585 |
| 2011/0213232 A1* | 9/2011 | Stevenson | A61B 5/04 600/373 |
| 2012/0029343 A1* | 2/2012 | Wasson | H01F 5/003 600/424 |
| 2012/0283552 A1* | 11/2012 | Hall | A61B 19/5244 600/424 |
| 2012/0310080 A1* | 12/2012 | Cunningham | A61B 5/055 600/423 |

FOREIGN PATENT DOCUMENTS

| | | |
|---|---|---|
| EP | 2 085 108 A2 | 5/2009 |
| JP | 2002-093649 | 3/2002 |
| JP | 2004 055973 | 2/2004 |
| JP | 2006-339460 | 12/2006 |
| JP | 2007-184618 | 7/2007 |

\* cited by examiner

METHOD FOR PRODUCING A MINIATURE ELECTROMAGNETIC COIL USING FLEXIBLE PRINTED CIRCUITRY

BACKGROUND OF THE INVENTION a. Field of the Invention

The present disclosure relates to a method of manufacturing a catheter or other elongate medical device having an electromagnetic coil, as a position sensor, using flexible printed circuitry.

b. Background Art

Many medical procedures require the introduction of specialized medical devices into and/or around the human body, for example, in and/or around the heart. In particular, there are a number of medical procedures that require the introduction of specialized devices including, but not limited to, catheters, dilators, and needles to areas, such as into the atria or ventricles to access the inner surface of the heart, or into the pericardial sac surrounding the heart to access the epicardial or outer surface of the heart. Catheters, guidewires, and access sheaths or introducers have been used for medical procedures for a number of years.

It is known to determine the position of such medical devices through the use of an electromagnetic field-based positioning system, which, in turn, typically involves equipping the medical device with an electromagnetic field sensing sensor. One known approach for producing such a sensor involves winding wire into an annular shape and then placing the resulting structure (i.e., the sensor) in the medical device. Such a sensor is then connected to an electrical cable in the medical device to transfer the detected signal to the positioning system for further processing. However, in light of the relatively small dimensions that such sensors must exhibit in order to fit into a typical medical device, fabrication of such sensors can be complicated, occupy undesirable amounts of radial space in the device, and/or involve fabrication methods that are more costly than desired.

There is therefore a need for an improved miniature electromagnetic field sensing sensor and method of making the same.

BRIEF SUMMARY OF THE INVENTION

Advantages of the methods and apparatus described, depicted, and claimed herein includes a micro-electromagnetic field coil sensor, suitable for use in medical devices, that is reduced in complexity of construction, is reduced in cost, and is thinner, thereby occupying a reduced amount of radial space.

This disclosure is directed to an elongate medical device configured for use with a positioning system. The device includes an elongate body with proximal and distal end portions. The device further includes a sensor assembly disposed at the distal end portion, which extends longitudinally relative to the body, at least at the distal end. The sensor assembly includes (i) an electrically insulative substrate; and (ii) a sensing coil having an electrically-conductive trace disposed on the substrate wherein the trace includes start and end leads. In an embodiment, the substrate may be a flexible printed circuit board (PCB), where the electrically conductive trace is patterned such that, when wrapped in a cylinder shape, forms a three-dimensional spiral coil configured to function as an electromagnetic field sensor. The coil is configured to produce a signal indicative of one or more characteristics of an electromagnetic field in which it is disposed. The start and end leads are configured for electrical connection to a positioning system, which in turn is configured to determine at least the position of the coil.

In another aspect, a method of fabricating an elongate medical device is provided, which method includes a number of steps. The first step involves providing an electrically-insulative, flexible substrate. The next step involves producing an electrically-conductive trace on the substrate, which trace includes start and end leads. The method further involves deforming the substrate into a desired shape, for example, a substantially cylindrical shape, such that the trace forms a three-dimensional sensing coil. In an embodiment, the method further includes the step of fixing (i.e., mechanically coupling) axially-extending edges of the substrate, which sets the desired shape described above. The fixing step may be one selected from the group comprising micro-welding, micro-soldering, micro-gluing and coupling through the use of micro-vias.

These and other benefits, features, and capabilities are provided according to the structures, systems, and methods depicted, described and claimed herein.

DETAILED DESCRIPTION OF THE INVENTION

Figure 1:
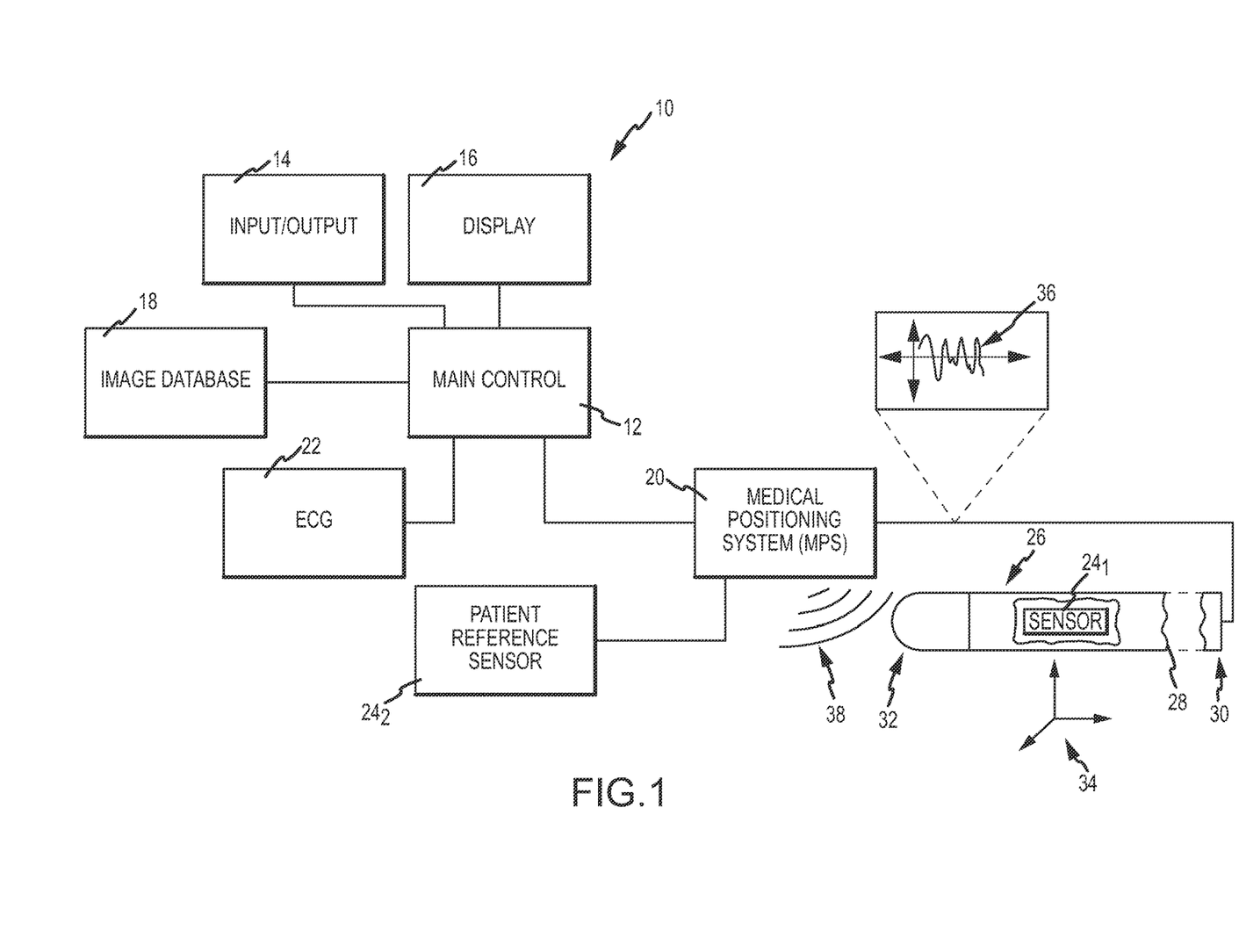
FIG. 1 is a diagrammatic and block diagram view of a system incorporating an MPS-enabled elongate medical device having an embodiment of a miniature electromagnetic field sensor formed using flexible printed circuitry.

Referring now to the drawings wherein like reference numerals are used to identify identical components in the various views, FIG. 1 is a diagrammatic and block diagram view of a system 10, a typical medical system (including a medical positioning system) in which a position sensing elongate medical device, such as a catheter, may be used.

Medical devices, such as catheters, can be configured to perform various tracking, navigation, orientation and other location functions, provided such devices are configured to allow a positioning system to determine its position and/or orientation. As described in the Background, such devices, in electromagnetic field-based positioning embodiments, are typically configured to include one or more sensors, for example, a field sensing coil. The availability of a position reading enables a wide range of enhanced functionality. As just one example, there is a desire to reduce a patient's exposure to x-rays, such as may be used in live fluoroscopy, at least for the purpose of navigating a medical device within the patient's body. Such a desire may be met by providing a medical device that includes a positioning sensor configured to cooperate with an external (i.e., external to the patient's body) positioning system that can determine the position of the device in three-dimensional space. With this position information, a navigation system can superimpose a representation of the medical device over a previously-obtained image (or series of images) of the region of interest in the patient's body or over a 3D image reconstructed geometry of the organ being investigated. A clinician may use the superimposed imaging for navigation purposes rather than using fluoroscopy full time. Thus, through the provision of a medical device with position sensing capability, the use of fluoroscopy may be reduced significantly (and thus also the accompanying X-ray exposure for the patient). Many additional functions can be performed based on position information obtained with respect to the medical device.

However, conventional implementations of field sensing sensors present several challenges. Typical construction techniques involve the step of winding wire into an annular shape and then installing the wound sensor in the device. In light of the small sizes (i.e., diameter) of typical invasive medical devices, conventional techniques are complicated, and are more costly than desired. In addition, such coils typically occupy more space (i.e., in the radial direction) than desired. As will be described in greater detail below, one or more of these challenges are overcome by fabrication of a miniature electromagnetic field sensing sensor using flexible printed circuitry.

Before proceeding to a detailed description of a flexible printed circuitry-based sensing coil, and its construction, a general description of an exemplary system in which a medical device having such a coil will be set forth. With continued reference to FIG. 1, system 10 as depicted includes a main electronic control unit 12 (e.g., one or more processors) having various input/output mechanisms 14, a display 16, an optional image database 18, a localization system such as a medical positioning system (MPS) 20, an electrocardiogram (ECG) monitor 22, one or more MPS sensors respectively designated $24_1$ and $24_2$ (i.e., shown as a patient reference sensor (PRS), which PRS can include, for example, three coils/sensors), and an MPS-enabled elongate medical device 26, which itself includes one or more of the above-described MPS location sensors, shown in exemplary fashion as having one such sensor $24_1$. An embodiment of sensor $24_1$ is constructed from flexible printed circuitry and will be described in connection with FIGS. 3-9. As shown, the elongate medical device 26 includes a main body 28 (e.g., a shaft), which includes a proximal end portion 30 and a distal end portion 32. It should be understood that as used with reference to a medical device herein, "distal" refers to an end that is advanced to the region of interest within a body while "proximal" refers to the opposite end that is disposed outside of the body and manipulated manually by a clinician or automatically through, for example, robotic controls.

Input/output mechanisms 14 may comprise conventional apparatus for interfacing with a computer-based control unit, for example, a keyboard, a mouse, a tablet, a foot pedal, a switch or the like. Display 16 may also comprise conventional apparatus.

Medical device 26 may find use in navigation applications that use imaging of a region of interest. Therefore system 10 may optionally include image database 18. Image database 18 may be configured to store image information relating to the patient's body, for example, a region of interest surrounding a destination site for medical device 26 and/or multiple regions of interest along a navigation path contemplated to be traversed by device 26 to reach the destination site. The image data in database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from ECG monitor 22. It should be understood that the foregoing are examples only and not limiting in nature. For example, the image database 18 may also include three-dimensional image data as well. It should be further understood that the images may be acquired through any imaging modality, now known or hereafter developed, for example X-ray, ultrasound, computerized tomography, nuclear magnetic resonance or the like as well as a 3D geometry generated by the MPS itself.

MPS 20 is configured to serve as the localization system and therefore is configured to determine positioning (localization) data with respect to one or more of MPS location sensors $24_i$ (where i=1 to n) and output a respective location reading. The location readings may each include at least one or both of a position and an orientation (P&O) relative to a reference coordinate system 34, which may be a three-dimensional reference coordinate system associated with MPS 20. For example, the P&O may be expressed as a position (i.e., a coordinate in three axes X, Y and Z) and an orientation (i.e., roll, yaw and pitch) of a magnetic field sensor (e.g., sensor 24) in a magnetic field relative to a magnetic field generator(s) or transmitter(s).

MPS 20 determines respective P&O readings in the reference coordinate system 34 based on capturing and processing signals (e.g., signal 36) received from the magnetic field sensors $24_i$ while such sensors are disposed in a controlled, low-strength electromagnetic field 38. From an electromagnetic perspective, these sensors develop a voltage that is induced on the sensor residing in a changing magnetic field. Sensors $24_i$ are thus configured to detect one or more characteristics of the magnetic field(s) in which they are disposed and generate a respective indicative signal (e.g., one shown—signal 36), which can be further processed by MPS 20 to obtain a respective P&O thereof.

FIG. 1 shows another MPS sensor, namely, patient reference sensor (PRS) $24_2$, which, if provided in system 10, is configured to provide a positional reference of the patient's body so as to allow motion compensation for gross patient body movements, imaging system movements and/or respiration-induced movements. PRS $24_2$ may be attached to the patient's manubrium sternum, a stable place on the chest, or another location that is relatively positionally stable. Like MPS sensor $24_1$, PRS $24_2$ is configured to detect one or more characteristics of the magnetic field in which it is disposed, and wherein MPS 20 provides a P&O reading indicative of the PRS's position and orientation in the reference coordinate system 34.

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit 12 for ECG synchronized play-back of a previously captured sequence of images (cine loop) stored in database 18. ECG monitor 22 and ECG-electrodes may both comprise conventional components.

Figure 2:
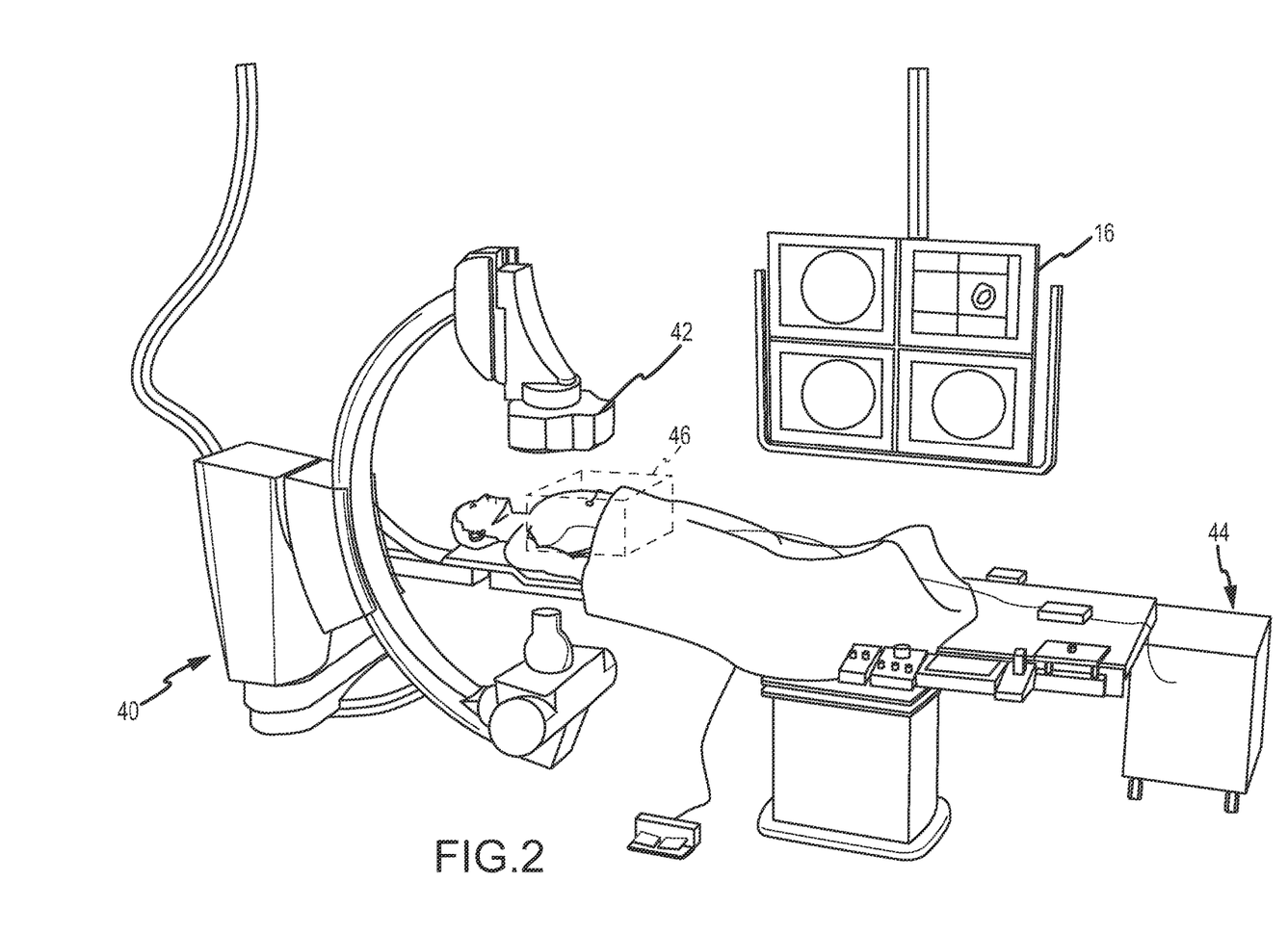
FIG. 2 is a diagrammatic view of the system of FIG. 1 in a catheter-lab environment.

FIG. 2 is a diagrammatic view of system 10 as incorporated into an exemplary catheter laboratory. System 10 is shown as being incorporated into a fluoroscopic imaging system 40, which may include commercially available fluoroscopic imaging components. MPS 20 includes a magnetic transmitter assembly (MTA) 42 and a magnetic processing core 44 for determining location (P&O) readings. MTA 42 is configured to generate the magnetic field(s) in and around the patient's chest cavity, in a predefined three-dimensional space identified as a motion box 46. MPS sensors 24$_i$ as described above are configured to sense one or more characteristics of the magnetic field(s) and when the sensors are in motion box 46, each generate a respective signal that is provided to magnetic processing core 44. Processing core 44 is responsive to these detected signals and is configured to calculate respective P&O readings for each MPS sensor 24$_i$ in motion box 46. Thus, MPS 20 enables real-time tracking of each sensor 24$_i$ in three-dimensional space. One exemplary embodiment of an MPS 20 will be described in greater detail below in connection with FIG. 8.

Figure 3:
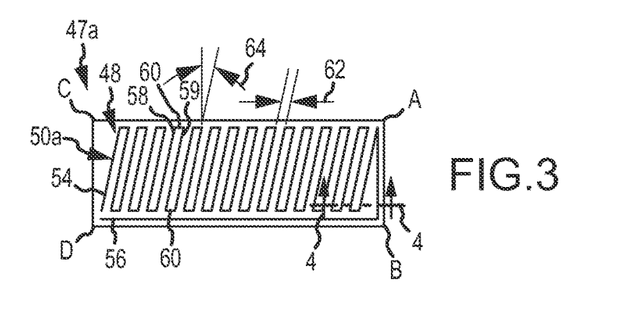
FIGS. 3-7 are various views of a first embodiment of the sensor of FIG. 1.

FIG. 3 is a top view of a sensing coil assembly 47a, which may be used as the sensor 24$_1$ in the medical device 26 shown in FIG. 1. Assembly 47a is shown in a preliminary stage of manufacture (i.e., a "flat" pattern). After further processing, the coil assembly 47a in final form may be disposed at a distal end portion (i.e., distal end portion 32 in FIG. 1) of device 26. The coil assembly 47a comprises flexible printed circuitry, as described in greater detail below. In the illustrative embodiment, the coil assembly 47a includes an electrically insulative, relatively flexible substrate 48 and an electrically conductive trace 50a disposed (i.e., "printed") on a first surface of substrate 48. It should be understood, however, that a flat pattern is exemplary only and not limiting in nature. Alternate embodiments may include additional approaches for forming conductive traces on a substrate, now known or hereafter developed, including forming such traces on non-flat substrates, for example, round or curved surfaces (i.e., three-dimensional in nature).

The substrate 48 may be generally rectangular in shape, having a longitudinal direction (i.e., long dimension) and a transverse direction (i.e., shorter dimension). As shown, substrate 48 has corners designated A, B, C and D. It should be understood, however, that the substrate may take a wide range of shapes and sizes, depending upon the determined trace pattern and sensor final form, as described in greater detail below.

Figures 4, 5, 6, 7:
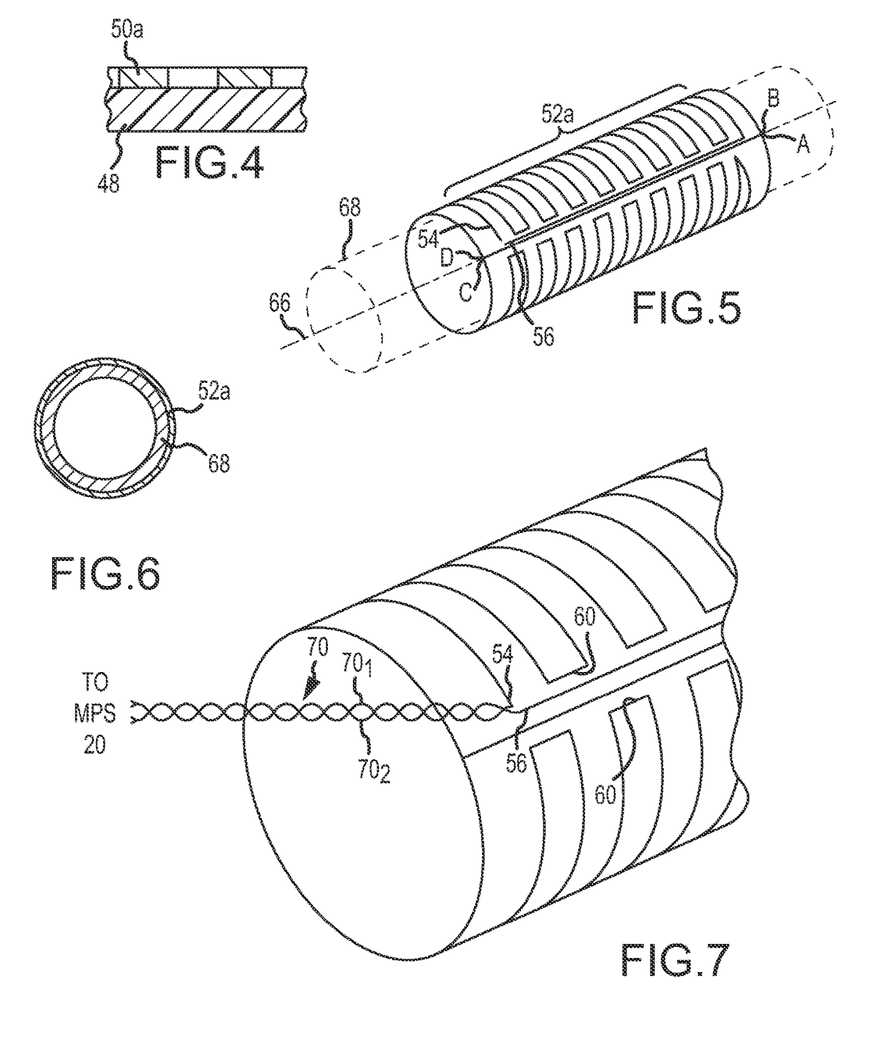

The trace 50a is arranged in a pattern configured to create a sensor 52a when the substrate 48 is folded or formed into a final shape (best shown in FIG. 5). Trace 50a includes a start lead 54 and an end lead 56, which leads are configured to provide a signal that is coupled to MPS 20. The trace 50a is electrically continuous between the start and end leads 54, 56. It should be understood that "start" and "end" designations are exemplary only and not limiting in nature. Further, although trace 50a is shown arranged such that both leads 54, 56 appear at the same longitudinal end (e.g., the longitudinally-proximal end of coil assembly 47a), other variations are possible (e.g., both leads can appear at the longitudinally distal end of coil assembly 47a, or leads 54, 56 can appear at respective proximal and distal ends of coil assembly 47a). In an illustrative embodiment, at least a portion of trace 50a is arranged and disposed on substrate 48 in a generally serpentine pattern, including a plurality of advancing sections 58, a plurality of returning sections 59, and a plurality of intervening bridge sections 60. The advancing and returning sections 58, 59 are generally transverse diagonals relative to substrate 48, are parallel to each other, and are separated from each other by a predetermined spacing 62. As shown, the spacing 62 is constant across the trace pattern. As further shown, the advancing and returning sections 58, 59 may be arranged at an angle 64 relative to a true transverse reference line. The angle 64 may be selected to facilitate formation of sensing coil when the substrate is folded.

In an embodiment, the predetermined spacing 62 may be less, and preferably much less, than a width of trace taken in the longitudinal direction, thereby defining a relatively low pitch (i.e., the spacing 62 between trace sections is relatively small compared to the width of the trace itself). In an embodiment, the width of trace 50a may be on the order of about several microns, while the predetermined spacing may be less than about five microns. It should be understood, however, that a wide range of configurations are possible in terms of trace width, spacing (i.e., spacing 62), angle 64, number of advancing and returning sections, number of layers having electrically-conductive traces, and the like, in accordance with desired detection characteristics.

FIG. 4 is a cross-sectional view of coil assembly 47a taken substantially along lines 4-4 in FIG. 3. As shown, substrate 48 has a predetermined thickness, which may be on the order of several microns. Substrate 48 may comprise conventional materials known in the art for use in flexible printed circuitry, such as a flexible plastic material selected from the group comprising polyimide, polyetheretherketone (PEEK), polyester, polyethylene terephthalate or a combination thereof. In some embodiments, substrate 48 may comprise KAPTON® or MYLAR® material commercially available from E.I. du Pont de Nemours and Company. It should be understood that variations are possible. The electrically-conductive trace 50a may comprise an electrically-conductive material, such as copper, although other electrically-conductive materials, such as platinum or gold, or combinations thereof (e.g., copper plated with platinum, gold, or silver) may be possible depending on the desired electrical characteristics. Conventional approaches and materials may be used for forming ("printing") a suitable pattern (trace 50a) on substrate 48. Moreover, although not shown, an over-layer of electrically-insulating material may be disposed over the electrically conductive trace pattern 50a.

FIG. 5 is an isometric view of the coil assembly 47a of FIG. 3, wrapped, folded, or otherwise formed into a desired, final shape to produce sensor 52a. In FIG. 5, the final, desired shape is a cylinder, having a circular shape in radial cross-section. In this embodiment, the folded coil assembly 47a extends longitudinally along an axis 66. It should be understood, however, that other shapes are possible (e.g., oval shape in radial cross section). The coil thus formed is responsive to a changing magnetic field passing through the projected area of the sensor 52a. In this regard, the sensor 52a will detect one or more characteristics of such field(s) and generate a signal indicative thereof.

A method of fabricating a miniature electromagnetic coil using flexible printed circuitry includes a number of steps. The first step involves providing an electrically insulative substrate, for example, as described above. The next step involves producing an electrically-conductive trace on the substrate in a predetermined pattern, for example, also as described above. The next steps involve folding the flexible substrate into the desired shape and then fixing the substrate in that shape. In the illustrative embodiment, the fixing step may involve adhering longitudinally-extending edges, one to another, for example, adhering edges BD and AC together. This step couples corner C to corner D and corner A to corner B. This step is operative to mechanically couple edges BD and AC, thereby fixing the substrate into the desired shape. The fixing step may be performed in accordance with conventional techniques, including without limitation micro-welding, micro-soldering, micro-gluing through the use of micro-vias, and the like.

As shown in phantom line in FIG. 5, the method of fabricating the sensor 52a may involve the use of a body portion 68 having a shape corresponding to the final desired shape of the sensor 52a. The body portion 68 may comprise a portion of the final sensor, for example, functioning as a support member (e.g., functioning like a conventional coil core). In the case where the body 68 is a coil core, it may comprise conventional materials, including magnetically-permeable materials to increase detection sensitivity or any other material that may act as a mechanical support structure. Alternatively, the body 68 may be a portion of the medical device body itself, e.g., a catheter shaft or layer thereof. Further, the body 68 may alternatively function as temporary fabrication aid (e.g., like a mandrel), which may be removed after the step of fixing the substrate in the desired shape is complete. Reference may be made to U.S. application Ser. No. 12/982,120 filed 30 Dec. 2010 entitled "ELECTROMAGNETIC COIL SENSOR FOR A MEDICAL DEVICE" (hereinafter the '120 Application) for a disclosure details regarding a sensor core, which application is copending and commonly owned with the assignee of the present invention. The '120 Application is hereby incorporated by reference in its entirety.

FIG. 6 is a cross-sectional view of the sensor 52a shown in FIG. 5. FIG. 6 shows the relationship between sensor 52a (as formed) and body portion 68. For example, the sensor 52a is disposed radially outwardly of body 68.

FIG. 7 is an enlarged, isometric view of FIG. 5, showing, in greater detail, sensor 52a. The configuration of the trace pattern is such that when the substrate 48 is folded into the desired shape, the bridge sections 60 generally face each other. In final form, the trace 50a produces has a three-dimensional, spiral coil substantially enclosing a projected, cross-sectional area. The sensor 52a includes a plurality of turns between the start and end leads. Sensor 52a is thus configured to function as a micro-electromagnetic sensing coil (sensor).

As further shown in FIG. 7, trace 50a can be configured so that start and end leads 54, 56 are located at a single longitudinal end of sensor 52a (e.g., proximal end) in the final configuration, thereby simplifying the coupling of the detected electrical signal to MPS 20 (best shown in FIG. 1 as detected signal 36). FIG. 7 further shows an electrical cable 70 configured to connect sensor 52a to a proximal end of device 26 (and then to MPS 20 using another cable section). Cable 70 may comprise a pair of conductors $70_1$, $70_2$ respectively coupled to start and end leads 54, 56, which extend within medical device 26 to a proximal end portion 30 thereof. Cable 70 may comprise an unshielded twisted-pair (TP) cable or alternately a shielded twisted-pair cable, or any other functionally equivalent signal cable known in the art. One or more of polymer, PTFE, and/or other appropriate materials may be included in cable 70 for electrical insulation purposes.

Figure 8:
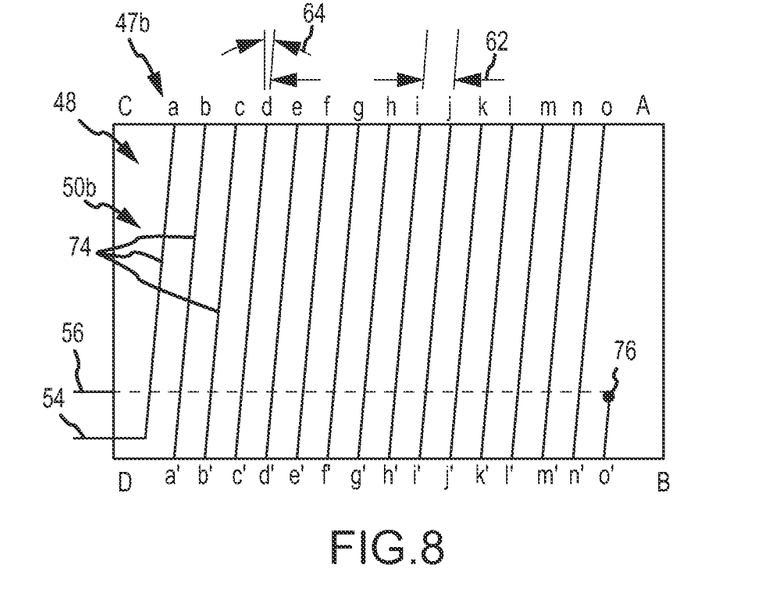
FIGS. 8-9 are top and isometric views, respectively, of a second embodiment of the sensor of FIG. 1.

FIG. 8 is a top view of a sensing coil assembly 47b, which may be used as the sensor $24_1$ or $24_2$ in the medical device 26 shown in FIG. 1. Assembly 47b is shown in a preliminary stage of manufacture (i.e., a "flat" pattern). Unless other stated, the assembly 47b may be the same as assembly 47a described above, and may be configured into sensor 52b in the same fashion as was used to configure assembly 47a into sensing sensor 52a.

The assembly 47b includes a substrate 48 and a trace pattern 50b that includes a plurality of advancing sections 74. Trace 50b can be generally of the same configuration as trace 50a, except as described below. Sections 74 of trace pattern 50b are initially electrically separate but are later electrically connected to form the electrically continuous windings of sensor 52 when the substrate 48 is folded.

Figure 9:
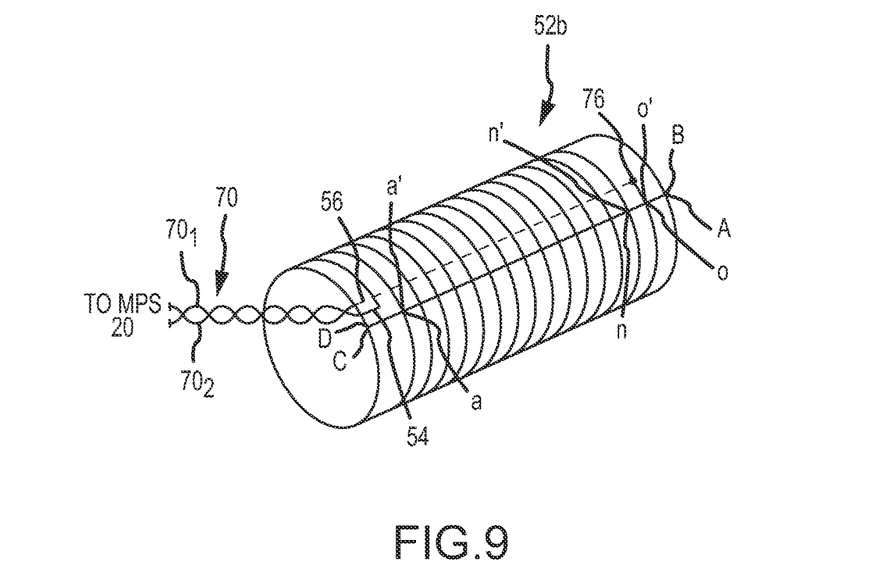

FIG. 9 is an isometric view of the coil assembly 47b of FIG. 8, wrapped, folded, or otherwise formed into a desired, final shape to produce sensor 52b. The connection concept involves aligning points a-a', b-b' and so on, and then electrically connecting the separate sections 74 at points a-a', b-b' and so on. A centric sensor 52b results after all the individual sections 74 have been electrically connected, as described above. The start and end leads are designated 54, 56, respectively. Just as with sensor 52a, the start and end leads 54, 56 can be connected to cable 70, in the same manner as described above.

As with the embodiment of FIGS. 3-7, the end lead 56 can be disposed on at the same axial end of the sensor 52b as the start lead 56. This can be accomplished by electrically insulating the returning end lead with respect to the "windings" (sections 74) across or over which it passes to reach the same end as the start lead 54. In the illustrative embodiment, the end lead 56 is passed through a via 76 and is routed on the opposing side of substrate 48 (i.e., opposite the side on which sections 74 are formed). Alternatively, return/end lead 56 can run across sections 74, provided, however, that return/end lead 56 is properly, electrically, insulated. The sensor 52b includes a plurality of turns between the start and end leads.

In still further embodiments, magnetic field sensitivity (pick-up intensity) can be increased by adding an increased number of windings, for example, by including additional layers to the printed circuit board (i.e., each layer contributing a certain number of "windings" formed by sections 74, and which can be electrically connected to winding formed on upper and lower layers in ways known in the art). Moreover, sensitivity (pickup intensity) can also be increased by adding a layer of ferromagnetic material, which has the same effect as configuring a core of ferromagnetic material for conventional sensing coils.

As for the remainder of device 26 not already described above, various approaches are known in the art for construction of medical devices, which may be used to fabricate medical device 26 that includes the inventive sensor 52a and/or sensor 52b.

The use of flexible printed circuitry construction techniques provides a simple and low cost approach to fabricate a miniature electromagnetic field sensing coil. Moreover, sensing coils consistent with the invention are also thinner than those fabricated using conventional techniques (i.e., occupying a reduced space in the medical device in which it is used, when taken in the radial direction).

Figure 10:
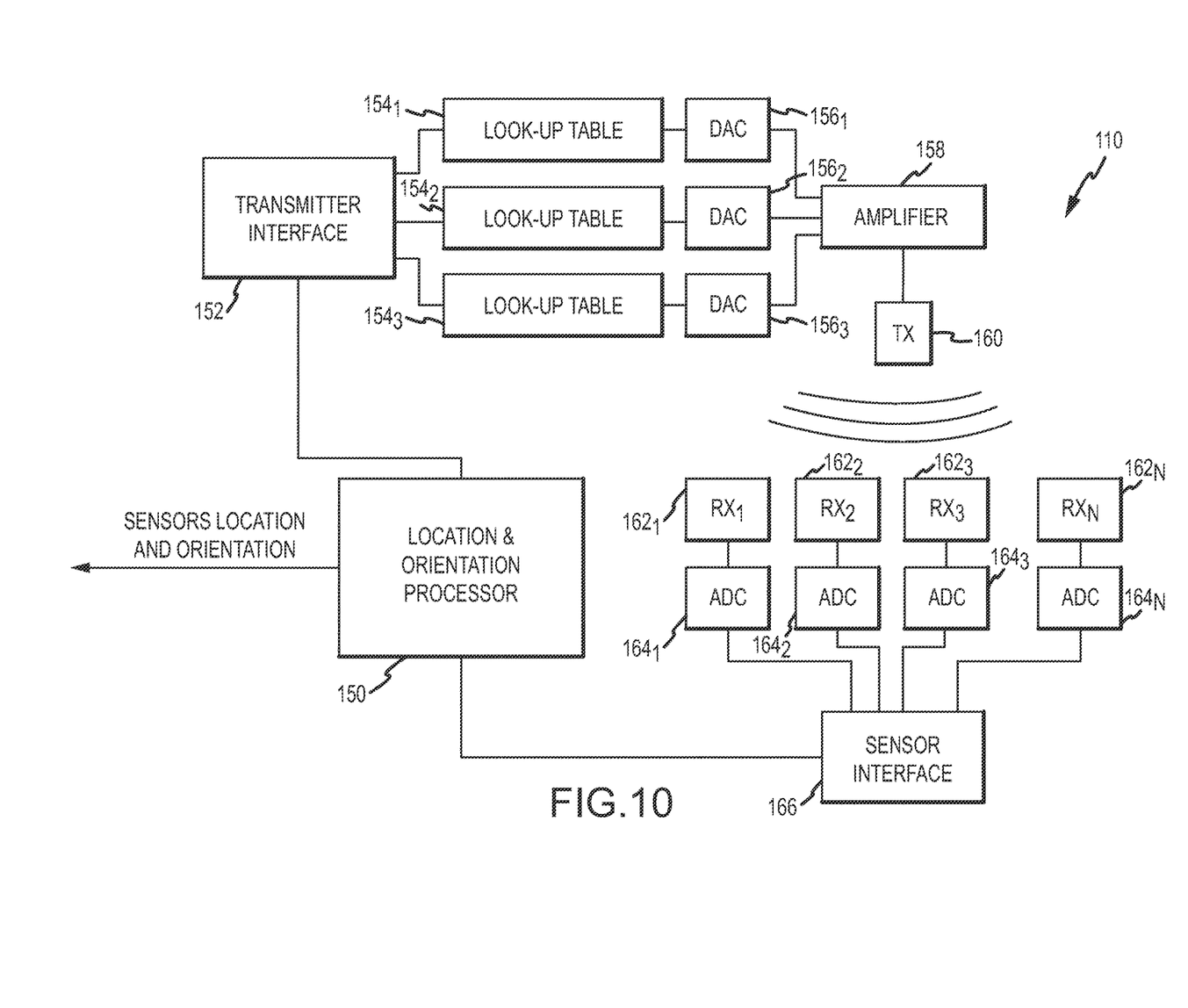
FIG. 10 is a schematic and block diagram view of an exemplary embodiment of a medical positioning system (MPS) as shown in block form in FIG. 1.

FIG. 10 is a schematic and block diagram of one exemplary embodiment of MPS 20, designated as an MPS 110. MPS 110 may be as seen by reference to U.S. Pat. No. 7,386,339, referred to above, and portions of which are reproduced below, which generally describes, at least in part, the gMPS™ medical positioning system commercially offered by MediGuide Ltd. of Haifa, Israel and now owned by St. Jude Medical, Inc. It should be understood that variations are possible, for example, as also seen by reference to U.S. Pat. No. 6,233,476 entitled MEDICAL POSI- TIONING SYSTEM, also hereby incorporated by reference in its entirety. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. Accordingly, the following description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166. It should be appreciated that sensor 24, comprising flexible printed circuitry may be used for one or more of the MPS sensors $162_1$, $162_2$, $162_3$ and $162_N$.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

MPS 110 may also be configured to include motion compensation functionality, for example to compensate for respiration-induced and other patient body motion, substantially as described in U.S. patent application Ser. No. 12/650,932, entitled "Compensation of Motion in a Moving Organ Using an Internal Position Reference Sensor", hereby incorporated by reference in its entirety.

It should be understood that system 10, including main control 12, as described above may include conventional processing apparatus known in the art, capable of executing pre-programmed instructions stored in an associated memory, all performing in accordance with the functionality described herein. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., proximal, distal, plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An elongate medical device comprising a body with proximal and distal end portions, comprising:
    a sensor disposed at said distal end portion and extending along a longitudinal axis, said sensor including
        (i) an electrically insulative substrate; and
        (ii) an electrically-conductive trace disposed on said substrate and comprising first and second leads, said substrate and trace being configured so as to form a plurality of turns between said first and second leads such that said trace produces a spiral coil enclosing a projected cross-sectional area and wherein said sensor being configured to detect a characteristic of an electromagnetic field and produce a signal indicative of said characteristic, both of said first and second leads appearing at one of a proximal end and a distal end of said sensor, and wherein at least a portion of said electrically-conductive trace is disposed on said substrate in a pattern that includes a plurality of first sections wherein said pattern is configured such that said first sections are angled with respect to said longitudinal axis;
    a cable comprising a pair of electrical conductors coupled to said first and second leads, said cable extending through said device to said proximal end portion thereof, said cable being configured for electrical connection to a positioning system.

2. The device of claim 1 wherein said substrate comprises a flexible printed circuit board (PCB).

3. The device of claim 1, wherein at least a portion of said electrically-conductive trace is disposed on said substrate in a serpentine pattern.

4. The device of claim 3, wherein said serpentine pattern further includes second sections with intervening bend sections.

5. The device of claim 4, wherein said serpentine pattern is configured such that said first and second sections are angled with respect to said longitudinal axis.

6. The device of claim 4 wherein said first and second sections are parallel.

7. The device of claim 1, wherein said pattern is configured such that transversely opposed end of said sections are aligned and electrically connected.

8. The device of claim 1 wherein said first and second leads appear at said proximal end of said sensor, said cable being connected to said first and second leads and extending through said device to said proximal end thereof.

9. The device of claim 1 wherein said substrate comprises a flexible plastic material selected from the group comprising polyimide, polyetheretherketone (PEEK), polyester, polyethylene terephthalate and a combination thereof.

10. The device of claim 1 wherein said substrate includes a plurality of layers, wherein at least a portion of said plurality of layers contains said electrically-conductive trace configured for use in said sensor.

11. The device of claim 10 wherein at least one of said layers comprises ferromagnetic material configured to increase sensing sensitivity.

12. The device of claim 1 wherein said sensor has a shape in radial cross-section selected from the group consisting of circular and oval.

13. A method of fabricating an elongate medical device, comprising the steps of:
providing an electrically-insulative, flexible substrate;
producing an electrically-conductive trace on said substrate, said trace comprising first and second leads both of which appear at one of a proximal end and a distal end of said sensor; and
deforming said substrate into a predetermined shape such that said trace forms a plurality of turns between said first and second leads such that said trace produces a spiral coil extending along a longitudinal axis enclosing a projected cross-sectional area wherein said trace forms a sensor configured to detect one or more characteristics of an electromagnetic field and produce a signal indicative thereof, and wherein at least a portion of said electrically-conductive trace is disposed on said substrate in a pattern that includes a plurality of first sections wherein said pattern is configured such that said first sections are angled with respect to said longitudinal axis; and
electrically connecting a cable comprising a pair of electrical conductors to said first and second leads wherein said cable extends through said device to a proximal end portion of said device and wherein said cable is configured for electrical connection to a positioning system.

14. The method of claim 13 wherein said step of producing the trace includes the sub-step of:
selecting said pattern for the trace from the group consisting of a continuous trace and a discontinuous trace comprising a plurality of separate sections.

15. The method of claim 13, further comprising the step of:
fixing axially-extending edges of said substrate.

16. The method of claim 15 wherein said fixing step is selecting from the group consisting of micro-welding, micro-soldering, micro-gluing and micro-vias.

17. An elongate medical device, comprising:
a body comprising proximal and distal end portions, said body comprising a body axis at said distal end portion; and
a longitudinally-extending sensor disposed at said distal end portion, said sensor extending along a sensor longitudinal axis, said sensor including
(i) an electrically insulative, flexible substrate; and
(ii) one or more electrically-conductive traces disposed on said substrate comprising first and second leads wherein both of said leads appear at one of a proximal end and a distal end of said sensor;
a cable comprising a pair of electrical conductors coupled to said first and second leads, said cable extending through said device to said proximal end portion thereof, said cable being configured for electrical connection to a positioning system that is configured to generate an electromagnetic field;
wherein said substrate and traces are configured so as to form a plurality of turns between said first and second leads such that said trace produces a spiral coil enclosing a projected cross-sectional area wherein said sensor that is configured to detect one or more characteristics of the electromagnetic field and produce an indicative signal responsive thereto, said signal being configured for use by the positioning system to determine a position of said sensor in a coordinate system in accordance with said signal, and wherein at least a portion of said one or more electrically-conductive traces is disposed on said substrate in a pattern that includes a plurality of first sections wherein said pattern is configured such that said first sections are angled with respect to said longitudinal axis.

18. The device of claim 17 wherein said leads appear at said proximal end of said sensor, said cable extending through said device to said proximal end portion thereof.

* * * * *